(12) United States Patent
Xie et al.

(10) Patent No.: US 11,262,463 B2
(45) Date of Patent: Mar. 1, 2022

(54) DETECTOR AND EMISSION TOMOGRAPHY DEVICE WITH THE DETECTOR

(71) Applicant: ZHONGPAI S&T (SHENZHEN) CO., LTD, Guangdong (CN)

(72) Inventors: Siwei Xie, Wuhan (CN); Xi Zhang, Wuhan (CN); Fenghua Weng, Shanghai (CN); Zhixiang Zhao, Shanghai (CN); Yunlong Zan, Shanghai (CN); Qiu Huang, Shanghai (CN)

(73) Assignee: ZHONGPAI S&T (SHENZHEN) CO., LTD, Guangdong (CN)

( * ) Notice: Subject to any disclaimer, the term of this patent is extended or adjusted under 35 U.S.C. 154(b) by 0 days.

(21) Appl. No.: 16/619,438

(22) PCT Filed: Jun. 4, 2018

(86) PCT No.: PCT/CN2018/089752
§ 371 (c)(1),
(2) Date: Dec. 4, 2019

(87) PCT Pub. No.: WO2018/223917
PCT Pub. Date: Dec. 13, 2018

(65) Prior Publication Data
US 2020/0158893 A1    May 21, 2020

(30) Foreign Application Priority Data

Jun. 5, 2017    (CN) .......................... 201710414287.6

(51) Int. Cl.
*G01T 1/202*    (2006.01)
*A61B 6/03*    (2006.01)
(Continued)

(52) U.S. Cl.
CPC ............ *G01T 1/2023* (2013.01); *A61B 6/037* (2013.01); *G01T 1/2006* (2013.01); *G01T 1/2018* (2013.01); *G01T 1/2985* (2013.01)

(58) Field of Classification Search
CPC ... G01T 1/2023; G01T 1/2006; G01T 1/2018; G01T 1/20181; G01T 1/1644;
(Continued)

(56) References Cited

U.S. PATENT DOCUMENTS

2010/0327168 A1*  12/2010  Yamada ................. A61B 6/037
                                                                       250/362
2013/0153774 A1    6/2013  Hughes et al.
(Continued)

FOREIGN PATENT DOCUMENTS

CN    101738631 A    6/2010
CN    102944891 A    2/2013
(Continued)

OTHER PUBLICATIONS

Translation of CN104237924A (Year: 2014).*
(Continued)

*Primary Examiner* — David P Porta
*Assistant Examiner* — Mamadou Faye
(74) *Attorney, Agent, or Firm* — Wolf, Greenfield & Sacks, P.C.

(57) ABSTRACT

The present invention provides a detector and an emission tomography device including the detector. The detector comprises: a scintillation crystal array comprising a plurality of scintillation crystals; and a photo sensor array, coupled to an end surface of the scintillation crystal array and comprising multiple photo sensors. At least one of the multiple photo sensors is coupled to a plurality of the scintillation crystals respectively. Surfaces of the plurality of the scintillation crystals not coupled to the photo sensor array are
(Continued)

each provided with a light-reflecting layer, and a light-transmitting window is disposed in the light-reflecting layer on a surface among the surfaces adjacent to a scintillation crystal coupled to an adjacent photo sensor. The detector has DOI decoding capability. No mutual interference occurs during DOI decoding, and decoding is more accurate. Moreover, with the number of photo sensor arrays being the same, the decoding capability for the scintillation crystals is significantly improved. With the number of photo sensor arrays being the same, the size of the photo sensor array and the number of channels of a readout circuit of the photo sensors of the present invention can be reduced by three-quarters to eight-ninths.

13 Claims, 14 Drawing Sheets

(51) Int. Cl.
    *G01T 1/20*     (2006.01)
    *G01T 1/29*     (2006.01)
(58) Field of Classification Search
    CPC ....... G01T 1/2002; G01T 1/202; A61B 6/037;
                                     A61B 6/4258; A61B 6/4275
    See application file for complete search history.

(56) References Cited

U.S. PATENT DOCUMENTS

2016/0209517 A1\*   7/2016   Cooke ............... H01L 27/14663
2018/0292548 A1\*  10/2018   Zhang ................... A61B 6/037

FOREIGN PATENT DOCUMENTS

| | | | |
|---|---|---|---|
| CN | 103592671 A | | 2/2014 |
| CN | 104237924 A | \* | 12/2014 |
| CN | 104237924 A | | 12/2014 |
| CN | 105190358 A | | 12/2015 |
| CN | 105277965 A | | 1/2016 |
| CN | 106562799 A | | 4/2017 |
| CN | 107121692 A | | 9/2017 |
| CN | 107272043 A | | 10/2017 |
| WO | WO 2016/062799 A1 | | 4/2016 |

OTHER PUBLICATIONS

International Search Report and Written Opinion for International Application No. PCT/CN2018/089752 dated Aug. 15, 2018.

\* cited by examiner

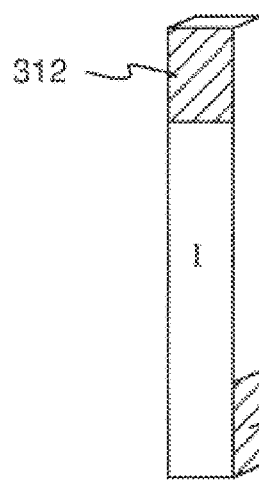 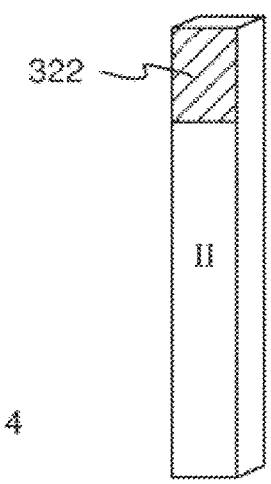 
FIG. 3A  FIG. 3B  FIG. 3C
FIG. 4

DETECTOR AND EMISSION TOMOGRAPHY DEVICE WITH THE DETECTOR

CROSS-REFERENCE TO RELATED APPLICATIONS

This application is a 35 U.S.C. § 371 National Phase filing of International Application No. PCT/CN2018/089752, filed on Jun. 4, 2018, entitled "DETECTOR AND EMISSION TOMOGRAPHY DEVICE WITH THE DETECTOR," which claims priority to and the benefit of Chinese Patent Application No. 201710414287.6, filed on Jun. 5, 2017, entitled "DETECTOR AND EMISSION TOMOGRAPHY DEVICE WITH THE DETECTOR." The entire contents of these applications are incorporated herein by reference in their entirety.

TECHNICAL FIELD

The present invention relates to an emission tomography system, and in particular to a detector for an emission tomography device and an emission tomography device including the detector.

BACKGROUND

An emission tomography device including a positron emission tomography device has been used for medical diagnosis. Taking a positron emission tomography device as an example, since an annihilating effect occurs between the positrons generated by the positron isotope decay and the negatrons in the human body, γ photons generated by the annihilating effect are detected by a detector using a composite detection method after injecting a compound labeled with positron isotopes into the human body.

The detector essentially consists of three parts, as shown in FIG. 1, i.e., a crystal matrix 110 consisting of discrete scintillation crystals, a glass photoconductive layer 120 and a photomultiplier tube (PMT) matrix 130. Surfaces of each of the scintillation crystals are coated with a light-reflecting material except for the surface (i.e., the bottom surface) of the scintillation crystal facing the PMT matrix 130. The 511 keV high-energy photons (i.e., γ photons) generated by the annihilating effect interact within the crystal matrix 110 and are converted into a group of visible photons. Since the surfaces of each of the scintillation crystals are coated with the light-reflecting material except for the bottom surface, the group of visible photons can only exit from the bottom surfaces of the scintillation crystals and pass through the glass photoconductive layer 120 into the PMT matrix 130. According to the intensity of a visible light signal collected by each of PMT units in the PMT matrix 130, which one of the scintillation crystals in the crystal matrix 110 the γ photons interact within can be calculated by using Anger Logic. This process is called crystal decoding. In this way, the information on the distribution of the isotopes in the human body can be obtained, and the reconstruction and combination operation is performed by a computer to obtain a three-dimensional tomographic image of the distribution of the labeled compound in the human body.

As shown in FIGS. 2A and 2B, since the γ photons have a certain attenuation length, they do not interact immediately after reaching a scintillation crystal 210, but interact according to a certain attenuation function, and are converted into a group of visible photons within a certain time period. When the γ photons enter the scintillation crystal 210 at a non-central position, that is, enter the scintillation crystal 210 at a certain angle, the γ photons enter another scintillation crystal 210 before interacting, and there is a deviation between γ photon generation position simulated by the calculated interaction position and the actual generation position, which is called the Depth Of Interaction (DOI) effect. FIGS. 2A and 2B are sectional views of existing flat and annular positron emission tomography devices, respectively. The solid line represents the actual flight path of the γ photons, and the dashed line represents the response straight line segment generated by the emission tomography device based on the detected signal. It can be seen that the depth effect greatly affects the accuracy of the γ photon generation position and path determined by the photo sensors during decoding, resulting in a decrease in the spatial resolution of the emission tomography device.

Existing methods for reducing the DOI effect are mainly divided into two categories, namely hardware calibration methods and software calibration methods. The hardware calibration methods include scintillation crystals delamination and coupling two optoelectronic conversion devices at the ends of the scintillation crystal array. With respect to the scintillation crystal delamination, since the crystals are not continuous, the junction of different crystal materials leads to a great photon loss and reduces the system sensitivity. The disadvantage of coupling two photoelectric conversion devices is that the number of channels of the detector is increased, resulting in a weakened intensity of the collected signal. The software calibration methods have a limited development due to its own limitations.

Therefore, it is necessary to propose a detector for an emission tomography device, and an emission tomography device including the detector, to obtain the information on the Depth Of Interaction of the scintillation crystals, and to improve spatial resolution of the tomography system.

SUMMARY

According to an aspect of the present invention, there is provided a detector for an emission tomography device, including: a scintillation crystal array including a plurality of scintillation crystals; and a photo sensor array, coupled to an end surface of the scintillation crystal array and including multiple photo sensors, wherein at least one of the multiple photo sensors is coupled to a plurality of the scintillation crystals respectively; wherein surfaces of the plurality of the scintillation crystals not coupled to the photo sensor array are each provided with a light-reflecting layer, and a light-transmitting window is disposed in the light-reflecting layer on a surface among the surfaces adjacent to a scintillation crystal coupled to an adjacent photo sensor.

Preferably, the plurality of the scintillation crystals includes a first scintillation crystal(s), and each of the first scintillation crystal(s) has two surfaces which are adjacent to first scintillation crystals coupled to adjacent photo sensors; and wherein the light-transmitting window includes a first light-transmitting window and a second light-transmitting window which are respectively disposed in the light-reflecting layers on the two surfaces of the first scintillation crystal to allow light to be received by adjacent photo sensors.

Preferably, $m_1 \times m_2$ photo sensors located in the central region of the photo sensor array are each coupled to $n_1 \times n_2$ first scintillation crystals, wherein $m_1$ and $m_2$ are each a positive integer, and wherein $n_1$ and $n_2$ are 1 or 2, and $n_1$ and $n_2$ are not equal.

Preferably, four photo sensors located at the corners of the photo sensor array are each coupled to one first scintillation crystal.

Preferably, $2m_1$ photo sensors located at the lateral edges of the photo sensor array are each coupled to $n_1 \times 1$ first scintillation crystals, and $2m_2$ photo sensors located at the longitudinal edges of the photo sensor array are each coupled to $1 \times n_2$ first scintillation crystals.

Preferably, the plurality of the scintillation crystals further includes a second scintillation crystal, and each of the second scintillation crystal(s) has one surface which is adjacent to a scintillation crystal coupled to an adjacent photo sensor, and a light-transmitting window is disposed on the one surface of the second scintillation crystal to allow the light to be received by the adjacent photo sensor.

Preferably, photo sensors located in the central region of the photo sensor array are each coupled to $n_1 \times n_2$ scintillation crystals, and four scintillation crystals among the $n_1 \times n_2$ scintillation crystals located at corners of a corresponding photo sensor are the first scintillation crystals, and $2(n_1-2)+2(n_2-2)$ scintillation crystals among the $n_1 \times n_2$ scintillation crystals located at the edges of the corresponding photo sensor are the second scintillation crystals, wherein $n_1$ and $n_2$ are 2 or 3.

Preferably, the four photo sensors located at the corners of the photo sensor array are each coupled to one first scintillation crystal.

Preferably, the photo sensors located at the lateral edges of the photo sensor array are each coupled to $n_1 \times 1$ scintillation crystals, and the photo sensors located at the longitudinal edges of the photo sensor array are each coupled to $1 \times n_2$ scintillation crystals, and wherein scintillation crystals among the $n_1 \times 1$ scintillation crystals and the $1 \times n_2$ scintillation crystals located at corners of a corresponding photo sensor are the first scintillation crystals, and scintillation crystals among the $n_1 \times 1$ scintillation crystals and the $1 \times n_2$ scintillation crystals located at the edges of a corresponding photo sensor are the second scintillation crystals.

Preferably, the photo sensors in the photo sensor array are each coupled to $n_1 \times 1$ or $1 \times n_2$ scintillation crystals, and scintillation crystals located at both ends of a corresponding photo sensor are the first scintillation crystals, and $(n_1-2)$ or $(n_2-2)$ scintillation crystals located in the middle of a corresponding photo sensor are the second scintillation crystals, wherein $n_1$ and $n_2$ are 2 or 3, and $n_1$ and $n_2$ are not equal.

Preferably, the light-transmitting window of the second scintillation crystal is disposed away from the photo sensor array.

Preferably, the plurality of the scintillation crystals further include a third scintillation crystal(s), and the third scintillation crystal(s) is not adjacent to any scintillation crystal coupled to an adjacent photo sensor, and the third scintillation crystal(s) is located at the corners of the scintillation crystal array, and/or located at the middle region of the photo sensor in the middle region.

According to another aspect of the present invention, there is further provided an emission tomography device, and the emission tomography device includes any of the detectors as described above.

In the detector provided by the present invention, the scintillation crystal array is directly coupled to the photo sensor array, and at least some of the photo sensors are coupled to multiple scintillation crystals. Since light-transmitting windows are disposed on the surfaces on the adjacent scintillation crystals coupled to the adjacent photo sensors, DOI decoding can be performed for the scintillation crystals by means of using two or four adjacent photo sensors. No mutual interference occurs during DOI decoding, and decoding is more accurate. Moreover, with the number of photo sensor arrays being the same, the decoding capability for the scintillation crystals is significantly improved. With the number of photo sensor arrays being the same, the size of the photo sensor array of the present invention can be reduced by three quarters to eight-ninths, and the number of channels of a readout circuit of the photo sensors can also be reduced by three-quarters to eight-ninths.

A series of simplified forms of concepts are introduced in the Summary of the Invention, which will be further described in detail in the Detailed Description. The Summary of the Invention is not intended to define the key features and essential technical features of the claimed technical solution, and is not intended to determine the scope of protection of the claimed technical solution.

Advantages and features of the present invention are described in detail below with reference to the accompanying drawings.

BRIEF DESCRIPTION OF THE DRAWINGS

The following drawings of the present invention are herein as part of the present invention to assist in understanding the present invention. The embodiments of the present invention and the description thereof are shown in the drawings for explaining the principle of the present invention. In the drawings:

FIGS. 3A-3C are schematic views of different types of scintillation crystals according to embodiments of the present invention;

FIG. 4 is a schematic view of a photo sensor array according to an embodiment of the present invention;

DETAILED DESCRIPTION

Figure 1:
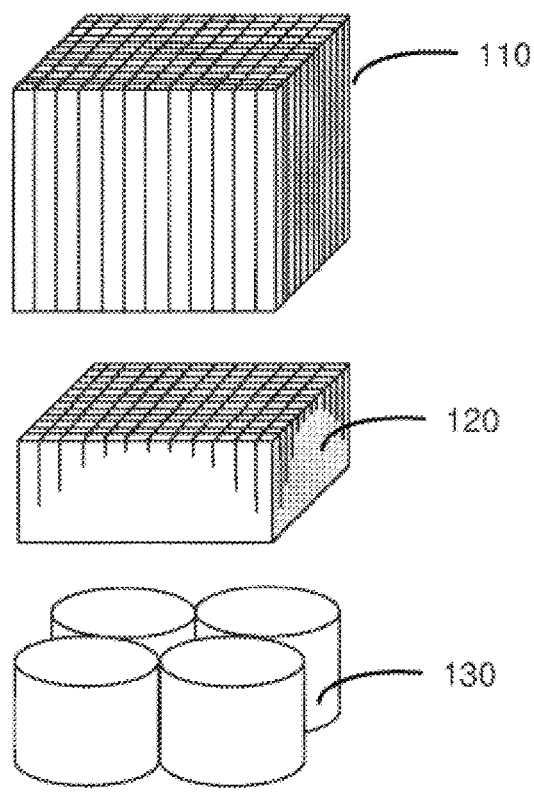
FIG. 1 is a schematic view of an existing detector for a positron emission tomography device.
Figure 2A:
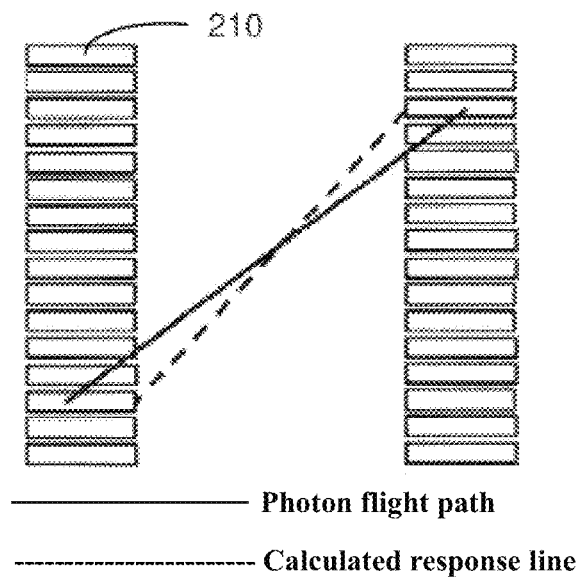
FIGS. 2A and 2B are sectional views of existing flat and annular positron emission tomography devices, respectively.
Figure 2B:
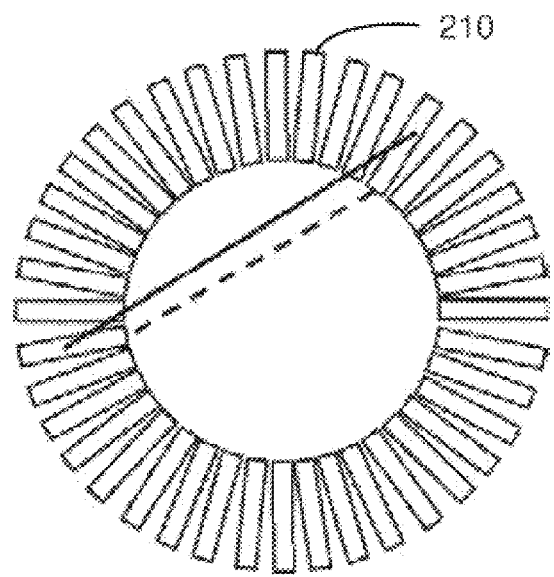

In the following description, numerous details are provided in order to provide a thorough understanding of the present invention. However, those skilled in the art will appreciate that the following description is only directed to the preferred embodiments of the present invention, and that the present invention can be practiced without one or more such details. Furthermore, in order to avoid obscuring the present invention, some of the technical features well known in the art have not been described.

The present invention provides a detector for an emission tomography device, including a scintillation crystal array and a photo sensor array. The photo sensor array is directly coupled to a bottom surface of the scintillation crystal array, and no photoconductive layer is required between the photo sensor array and the scintillation crystal array. Illustratively, the scintillation crystal array and the photo sensor array can be directly coupled together by means of coupling agent such as optical glue, or by means of air coupling or the like.

The scintillation crystal array includes a plurality of scintillation crystals arranged in an array. The scintillation crystal may be one of thallium-activated sodium iodide crystal, bismuth germanate crystal, lutetium silicate crystal, and lutetium-yttrium silicate crystal. Similar to the conventional manner, surfaces of the plurality of the scintillation crystals not coupled to the photo sensor array are each provided with a light-reflecting layer. However, unlike the conventional manner, a light-transmitting window is disposed in the light-reflecting layer on a surface among the surfaces of the scintillation crystals adjacent to the scintillation crystal coupled to the adjacent photo sensor (i.e., the side surface), and thus a group of the low-energy photons (e.g., a 420 nm photon group) produced after high-energy photons (e.g., 511 keV γ photons) interact in a scintillation crystal is guided to enter the adjacent scintillation crystal through the light-transmitting window, and then is collected by the photo sensor to which the adjacent scintillation crystal is coupled. In this way, for a scintillation crystal, which one of the scintillation crystals of the scintillation crystal array the high-energy photons interact within (crystal position decoding), and the Depth Of Interaction in the scintillation crystal (DOI decoding) can be calculated from the light distribution detected by multiple photo sensors.

The light-reflecting layer may be formed on the scintillation crystal by means of coating, plating (e.g., spraying or silver plating), or pasting a light-reflecting material, for example. The light-reflecting material is, for example, an Enhanced Specular Reflector (ESR), a Teflon light-reflecting material produced by DuPont, barium sulfate and the like. Furthermore, the light-reflecting layer may also be a light-reflecting material disposed between adjacent scintillation crystals. Two adjacent scintillation crystals share the same light-reflecting layer.

The photo sensor array is coupled to the bottom surface of the scintillation crystal array. The photo sensor array includes multiple photo sensors arranged in an array. The photo sensors may be one or more of a photomultiplier tube (PMT), a position sensitive photomultiplier tube (PS-PMT) and a silicon photomultiplier tube (SiPM). Since the size of the SiPM is small and is usually an integral multiple of the side length of the scintillation crystals, it is preferable to form the photo sensor array by using SiPM. Some or all of the photo sensors in the photo sensor array are correspondingly coupled to a plurality of scintillation crystals. The size of the photo sensor is an integer multiple of the size of the scintillation crystals so that a single photo sensor can be couple to a p×q scintillation crystal array, where p and q are both positive integers.

Depending on the positions of the scintillation crystals in the array, the scintillation crystals can be broadly divided into three types, namely a first scintillation crystal, a second scintillation crystal and a third scintillation crystal. The main difference between these three types of scintillation crystals includes whether or not there is some light-transmitting windows and the number of the light-transmitting windows. Each of the light-transmitting windows is disposed in a light-reflecting layer on a surface of a scintillation crystal adjacent to a scintillation crystal coupled to an adjacent photo sensor.

FIG. 3A shows a first scintillation crystal I, which is provided with a light-transmitting window (a region indicated by a hatched line) on two adjacent surfaces thereof, that is, a first light-transmitting window 312 and a second light-transmitting window 314. Illustratively, as shown in FIG. 3A, the first light-transmitting window 312 may be disposed near the top end of the first scintillation crystal I, and the second light-transmitting window 314 may be disposed near the bottom end of the first scintillation crystal I. However, the positions of the first light-transmitting window 312 and the second light-transmitting window 314 in the height direction are not limited in the present invention. Furthermore, the size and shape of the light-transmitting windows are also not limited to those as shown in the drawings. The first scintillation crystal I is typically disposed at the corner C of the photo sensor to which the first scintillation crystal I is coupled, and has two surfaces adjacent to the scintillation crystals coupled to the adjacent photo sensors 420 and 440, as shown in FIG. 4. FIG. 4 shows a 2×2 photo sensor array including photo sensors 410, 420, 430 and 440. The "corner of the photo sensor" mentioned above refers to a position that can be adjacent to three photo sensors, such as position C. The edge and central region of the photo sensor will also be mentioned below. The "edge of the photo sensor" refers to a position that can only be adjacent to one photo sensor, such as position E. The "central region of the photo sensor" refers to a position that is not adjacent to any photo sensor, such as position O.

FIG. 3B shows a second scintillation crystal II which is provided with a light-transmitting window 322 on one surface. The light-transmitting window 322 may be disposed near the top end of the second scintillation crystal II as shown in FIG. 3B, or may be disposed near the bottom end of the second scintillation crystal II, or may be disposed at the middle position of the second scintillation crystal II. Preferably, however, the light-transmitting window 322 is disposed near the top end of the second scintillation crystal II. Since the group of photons moves substantially from top to bottom in the scintillation crystal, the light-transmitting window is disposed at the upper portion to increase the probability that the group of photons generated by interacting at the upper portion directly exits from the light-transmitting window, thereby avoiding the inability to distinguish the spots respectively formed by the group of photons generated by interacting at the upper portion and lower portion to facilitate DOI decoding. The second scintillation crystal II is typically disposed at the edge of the photo sensor to which the second scintillation crystal II is coupled, such as position E in FIG. 4. However, since position C1 can only be adjacent to one photo sensor, the second scintillation crystal II is also coupled at position C1. Starting from the purpose of providing the light-transmitting window (i.e., the group of the visible photons is guided to enter the adjacent scintillation crystal through the light-transmitting window and then is received by the photo sensor to which the adjacent scintillation crystal is coupled), it is not difficult to understand the reason why the second scintillation crystal II is coupled at position C1.

FIG. 3C shows a third scintillation crystal III, and the light-reflecting layer of the scintillation crystal III is not provided with any light-transmitting window. The scintillation crystal III is typically disposed at a position of the photo sensor to which the scintillation crystal III is coupled, and the position is not adjacent to any other photo sensor, such as the four corners C2 of the photo sensor array, or the center O of the photo sensor to which the scintillation crystal III is coupled, as shown in FIG. 4. Even if the scintillation crystals at these positions are provided with a light-transmitting window, the visible photons passing through the light-transmitting window are only received by the photo sensor to which the scintillation crystal is coupled, and DOI decoding in this case is inefficient, which is not a preferred embodiment of the present invention. Since the third scintillation crystal III does not have a light-transmitting window, it does not have DOI decoding capability.

The scintillation crystal array may include one or more of the above three types of the scintillation crystals. By means of using the scintillation crystal array in conjunction with the photo sensor array, a detector having DOI decoding capability with a simple structure (including fewer photo sensors) can be obtained. Several preferred embodiments of the present invention will be described in detail below with reference to the accompanying drawings.

Figure 5A:
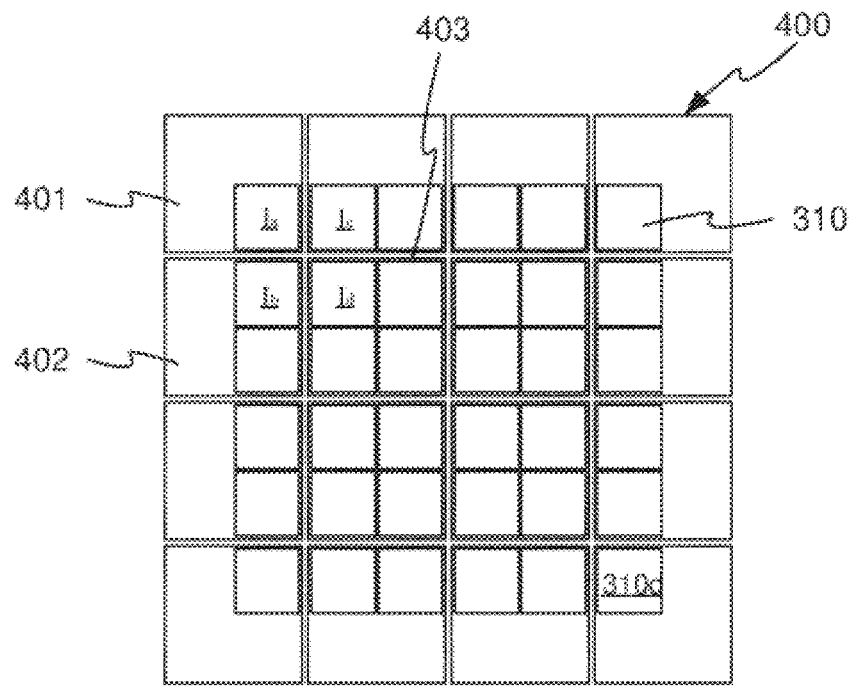
FIGS. 5A and 5B are schematic views showing a layout of a scintillation crystal array and a photo sensor array according to a set of embodiments of the present invention.
Figure 5B:
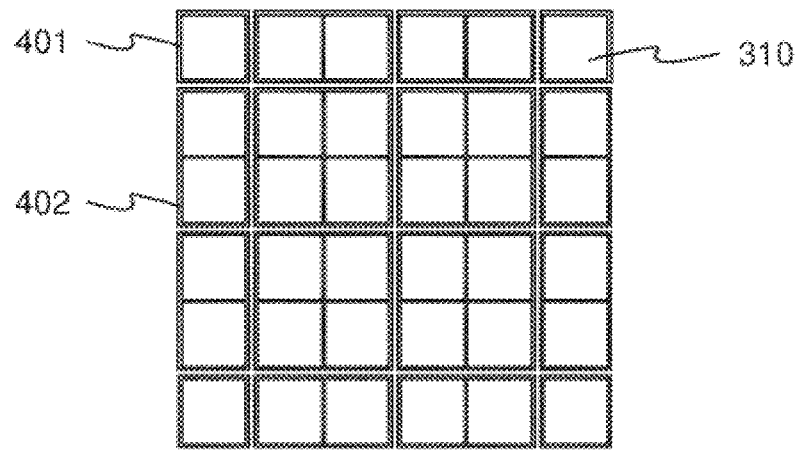

FIGS. 5A-5B show two preferred layouts in which the scintillation crystal array includes only the first scintillation crystals I. The single photo sensor mentioned above has three kinds of positions, namely the corners, the edges and the central region, for coupling different types of scintillation crystals. Similarly, the photo sensor array also has three kinds of positions, namely the corners, the edges and the central region. As shown in FIG. 5A, a photo sensor 401 is located at a corner of a scintillation crystal array 400, a photo sensor 402 is located at an edge of the scintillation crystal array 400, and a photo sensor 403 is located in the central region of the scintillation crystal array 400. As shown in FIG. 5A, each of the first scintillation crystals I is coupled at the corners of the photo sensors 401, 402, and 403, and each of the first scintillation crystals I has two surfaces adjacent to the first scintillation crystals coupled to the adjacent photo sensors. The first scintillation crystal $I_a$ coupled to the photo sensor 401 is adjacent to the first scintillation crystals $I_b$ and $I_c$ coupled to the photo sensor 402 located at the edges in two directions, and the first light-transmitting window and the second light-transmitting window of the first scintillation crystal $I_a$ face the first scintillation crystal $I_c$ and the first scintillation crystal $I_b$, respectively. Similarly, the first scintillation crystal $I_c$ located at the edge is adjacent to the first scintillation crystal $I_a$ and is adjacent to the first scintillation crystal $I_d$ coupled to the photo sensor 403 located in the central region. The light-transmitting windows of the first scintillation crystal $I_c$ are disposed on two adjacent surfaces. Similarly, the light-transmitting windows of the first scintillation crystal $I_b$ are disposed on the surfaces adjacent to the first scintillation crystal $I_a$ and the first scintillation crystal $I_d$; and the light-transmitting windows of the first scintillation crystal $I_d$ are disposed on the surfaces adjacent to the first scintillation crystal $I_b$ and the first scintillation crystal The light-transmitting windows on the two adjacent surfaces of the different scintillation crystals are disposed oppositely such that light can be received by the adjacent photo sensors through the light-transmitting windows.

FIG. 5A shows only a 4×4 photo sensor array composed of photo sensors, but those skilled in the art will appreciate that this layout can be applied to a photo sensor array of 2×2, 2×3, 3×3, 2×4, 3×4, 4×5, 5×5 and so on. In the photo sensor array of such a layout, $m_1 \times m_2$ photo sensors located in the central region are each coupled to four first scintillation crystals arranged in a 2×2 arrangement. Four photo sensors located at the corners are each coupled to one first scintillation crystal. $2m_1$ photo sensors located at the lateral edges are coupled to 2 first scintillation crystals, and $2m_2$ photo sensors located at the longitudinal edges are coupled to 2 first scintillation crystals, where $m_1$ and $m_2$ are both positive integers. In FIG. 5A, both $m_1$ and $m_2$ are 2.

Furthermore, the scintillation crystals coupled to the single photo sensor can also be extended to $n_1 \times n_2$, where $n_1$ or $n_2$ is 1 or 2. Likewise, the four photo sensors located at the corners of the photo sensor array may each be coupled to one first scintillation crystal. However, the $2m_1$ photo sensors located at the lateral edges of the photo sensor array may each be coupled to $n_1 \times 1$ first scintillation crystals, and the $2m_2$ photo sensors located at the longitudinal edges of the photo sensor array may each be coupled to $1 \times n_2$ first scintillation crystals.

Multiple photo sensors with the same size are employed in FIG. 5A, and the size of the photo sensors located at the corners and edges can be modified to accommodate the size of the scintillation crystal array, and thus the embodiment shown in FIG. 5B is provided. The photo sensor 401 at the corner is adapted to the size of one scintillation crystal I. The photo sensor 402 at the edge is adapted to the size of two scintillation crystals I.

Figure 6:
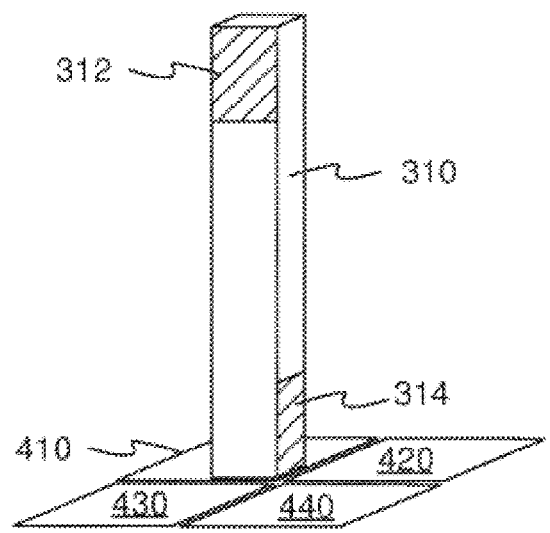
FIG. 6 is a schematic view illustrating DOI decoding for the layout shown in FIGS. 5A and 5B.

The DOI decoding method of the layout shown in FIGS. 5A-5B will be described below with reference to FIG. 6. The first scintillation crystal I is provided with a first light-transmitting window 312 and a second light-transmitting window 314 on two adjacent surfaces. When the γ photons interact in the first scintillation crystal I, most of the visible photons propagate in the scintillation crystal due to the reflection by the light-reflecting layer, and are received by the photo sensor 410 to obtain a two-dimensional position of the γ photons. There is also a small amount of visible photons that propagates through the first light-transmitting window 312 and the second light-transmitting window 314 to the adjacent first scintillation crystals, respectively, and they are correspondingly received by the photo sensor 430 and the photo sensor 420. The closer the interaction position of the γ photons is to the light-transmitting windows, the more the photon energy is received in the photo sensor 430 and the photo sensor 420. There is a limit value for the photon energy. The photo sensor 440 may also receive a very small amount of visible photons, and thus the signal is the weakest. The Depth Of Interaction of the γ photons can be derived from the intensity ratio of the signals of the adjacent photo sensors 410-440. Similarly, decoding operations are also performed in the manner described above with respect to the first scintillation crystals at other positions.

Figure 7:
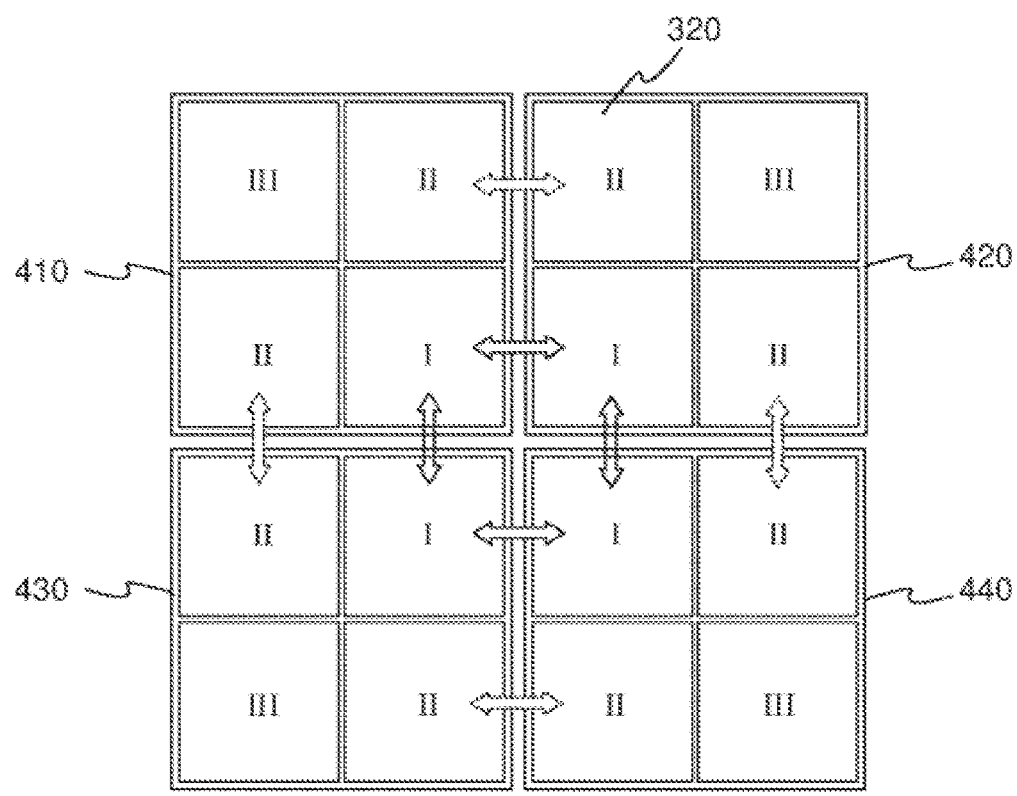
FIG. 7 is a schematic view showing a layout of a scintillation crystal array and a photo sensor array according to another embodiment of the present invention.
Figures 8A, 8B, 8C, 8D:
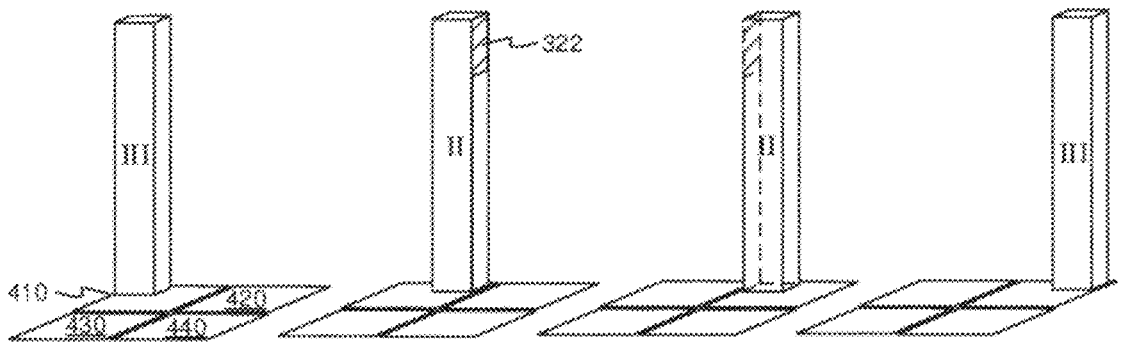
FIGS. 8A-8Q are schematic views illustrating DOI decoding for the layout shown in FIG. 7.

According to another embodiment of the present invention, the scintillation crystal array may further include a second scintillation crystal II having one surface adjacent to the scintillation crystal coupled to the adjacent photo sensor. A light-transmitting window is disposed on the one surface of the second scintillation crystal II to allow light to be received by the adjacent photo sensors. Illustratively, the scintillation crystal array and the photo sensor array can be of the layout shown in FIG. 7. FIGS. 8A-8Q illustrates the DOI decoding of the layout shown in FIG. 7. FIG. 7 and FIGS. 8A-8Q illustrate the principle of the layout by taking four photo sensors 410, 420, 430, and 440 as an example. However, based on this principle, those skilled in the art can extend the 2×2 photo sensor array to a photo sensor array of 1×3, 2×3, 3×3, 2×4, 3×4, 4×4, 4×5, 5×5 and so on.

In the layout shown in FIGS. 7, 8A-8Q, the second scintillation crystals II are coupled at the edges of the photo sensor array, and each of these scintillation crystals at the edges has only one surface adjacent to the scintillation crystal coupled to the adjacent photo sensor. A light-transmitting window is disposed on this surface. In FIG. 7, the light-transmitting window is indicated by double-headed arrows, where solid arrows indicate the first light-transmitting window and the second light-transmitting window of the first scintillation crystal I; and dashed arrows indicate the light-transmitting window of the second scintillation crystal II.

Furthermore, a third scintillation crystal III is also included in the layout shown in FIGS. 7, 8A-8Q, which is not adjacent to any scintillation crystal coupled to the adjacent photo sensor, and thus no light-transmitting window is required to be disposed on the third scintillation crystal III, and thus the third scintillation crystal III has no crystal decoding capability. In other embodiments not shown, the third scintillation crystal III may also not be included.

The DOI decoding for each of the scintillation crystals in the layout will be described below with reference to FIGS. 8A-8Q. Since the processes of the DOI decoding for the same type of scintillation crystals included in this layout are similar, the DOI decoding for only several scintillation crystals is selectively described in detail, and the DOI decoding for the remaining scintillation crystals can also be seen in Table 1.

A third scintillation crystal III is used in the first row and first column (as shown in FIG. 8A). When γ photons are incident into the third scintillation crystal III and are attenuated to generate a group of visible photons, the group of visible photons is reflected by the light-reflecting layer and propagates into the photo sensor 410 to which the third scintillation crystal III is coupled. Since the third scintillation crystal III is not provided with any light-transmitting window, ideally, only the photo sensor 410 can receive a light signal, and the remaining photo sensors 420-440 receive no signal, and thus a two-dimensional interaction position of the γ photons may be obtained, and DOI decoding cannot be performed.

A second scintillation crystal II is used in the first row and second column (as shown in FIG. 8B). The second scintillation crystal II is provided with one light-transmitting window and therefore a pair of photo sensors is used for decoding. When γ photons interact in the second scintillation crystal II, most of the visible photons propagate in the second scintillation crystal II and are received by the photo sensor 410 to obtain a two-dimensional interaction position of the γ photons. A small portion of the visible photons is incident into an adjacent scintillation crystal (FIG. 8C) through the light-transmitting window 322 and is received by the photo sensor 420. The closer the interaction position of the γ photons is to the light-transmitting window, the more the visible photons are received by the photo sensor 420. There is a limit value for the visible photons received by the photo sensor 420. The light signal received by the photo sensor 410 is stronger, the light signal received by the photo sensor 420 is weaker, and the photo sensors 430 and 440 receive no signal. The Depth Of Interaction can be derived from the intensities of the signals received by the photo sensors.

Figures 8E, 8F, 8G, 8H:
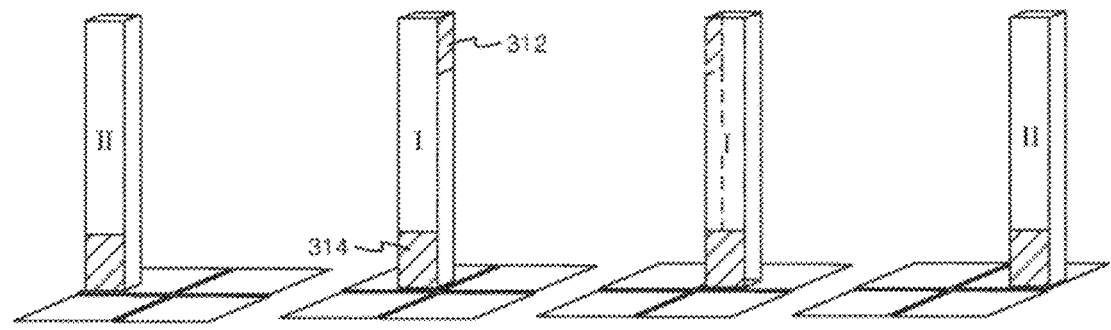

A first scintillation crystal I is used in the second row and second column (shown in FIG. 8F). The first scintillation crystal I has a side surface adjacent to the photo sensor 420 and a side surface adjacent to the photo sensor 430, and the two side surfaces are provided with a first light-transmitting window 312 and a second light-transmitting window 314 respectively. Thus depth decoding is performed by using a set of four photo sensors. Specifically, when γ photons interact within the first scintillation crystal I, most of the visible photons propagate in the first scintillation crystal I and are received by the photo sensor 410 to obtain a two-dimensional position of the γ photons. Some of the visible photons are incident into an adjacent scintillation crystal (FIG. 8G) through the first light-transmitting window 312 and are received by the photo sensor 420; and some of the visible photons are incident into the adjacent scintillation crystal (FIG. 8G) through the second light-transmitting window 314 and are received by the photo sensor 430. The closer the interaction position of the γ photons is to the window position, the more the photon energy is received by the photo sensors 420 and 430. Therefore, the light signal received by the photo sensor 410 is the strongest, the light signal received by the photo sensor 440 is the weakest, and the light signals received by the photo sensors 420 and 430 are moderate. The Depth Of Interaction of the γ photons can be derived from the intensity ratio of signals received by more of photo sensors 410-440.

It can be seen from the above that when the high-energy photons are incident into the crystals at different positions, the four adjacent sensors may output different encoded signals. By comparing the presence/absence and the intensities of signals of the four sensors, the crystal positions onto which the high-energy photons are incident can be accurately calculated.

The DOI decoding for each of the scintillation crystals is performed with taking the adjacent photo sensors as a group, and the DOI decoding for the scintillation crystal is performed by comparing the intensities of the light signals received by the photo sensors in the group. Therefore, the intensities of the light signals indicated in Table 1 are all for the same scintillation crystal, and the intensities of the light signals of different scintillation crystals are not compared and discussed in the present invention.

TABLE 1

Figures 8I, 8J, 8K, 8L:
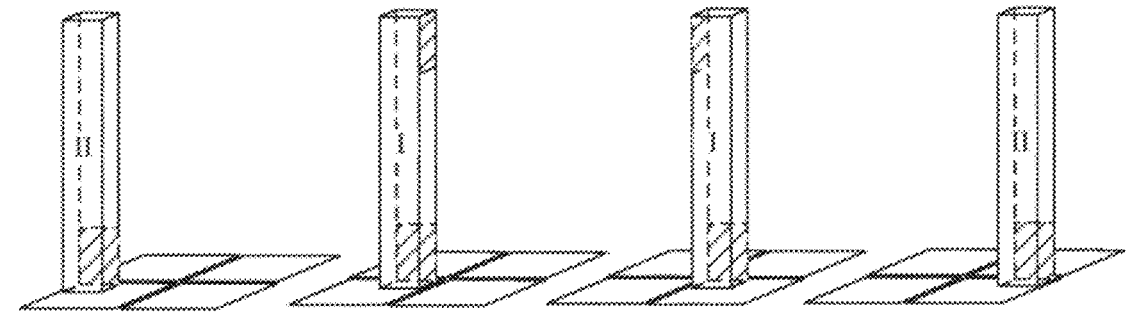
Figures 8M, 8N, 8P, 8Q:
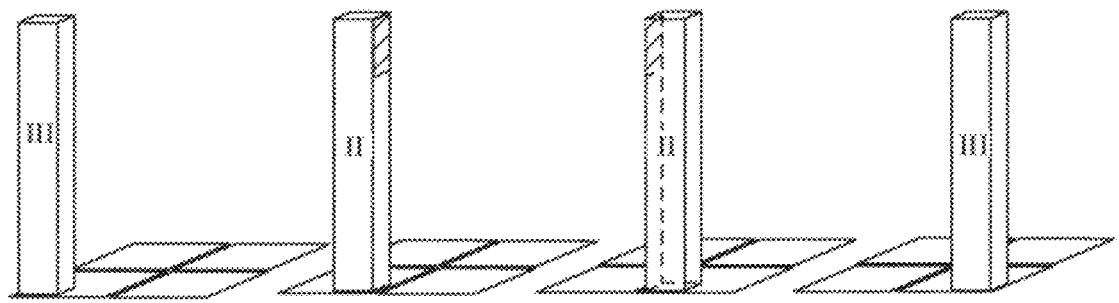

| Positions of the scintillation crystals | | Light signals received by the photo sensors | | | |
|---|---|---|---|---|---|
| Row | Column | 410 | 420 | 430 | 440 |
| 1 | 1 (FIG. 8A) | strong | — | — | — |
|  | 2 (FIG. 8B) | strong | weak | — | — |
|  | 3 (FIG. 8C) | weak | strong | — | — |
|  | 4 (FIG. 8D) | — | strong | — | — |
| 2 | 1 (FIG. 8E) | strong | — | weak | — |
|  | 2 (FIG. 8F) | strong | moderate | moderate | weak |
|  | 3 (FIG. 8G) | moderate | strong | weak | moderate |
|  | 4 (FIG. 8H) | — | strong | — | weak |
| 3 | 1 (FIG. 8I) | weak | — | strong | — |
|  | 2 (FIG. 8J) | moderate | weak | strong | moderate |

TABLE 1-continued

| Positions of the scintillation crystals | | Light signals received by the photo sensors | | | |
|---|---|---|---|---|---|
| Row | Column | 410 | 420 | 430 | 440 |
| | 3 (FIG. 8K) | weak | moderate | moderate | strong |
| | 4 (FIG. 8L) | — | weak | — | strong |
| 4 | 1 (FIG. 8M) | — | — | strong | — |
| | 2 (FIG. 8N) | — | — | strong | weak |
| | 3 (FIG. 8P) | — | — | weak | strong |
| | 4 (FIG. 8Q) | — | — | — | strong |

In the embodiment provided above, one photo sensor is coupled up to four scintillation crystals. In fact, one photo sensor may also be coupled to more scintillation crystals or less scintillation crystals, for example, 2×3 scintillation crystals, 3×3 scintillation crystals, 1×2 scintillation crystals or 1×3 scintillation crystals.

Figure 9:
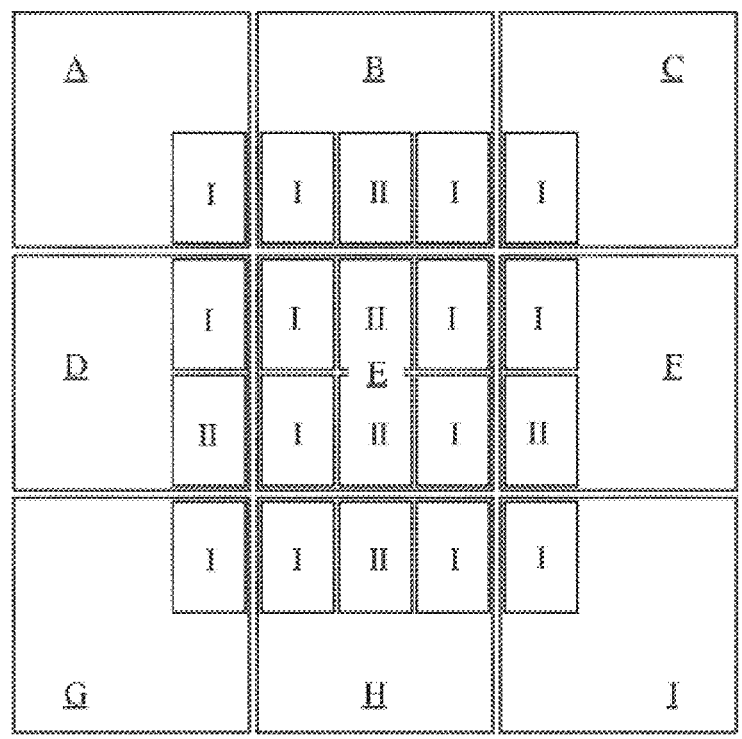
FIG. 9 is a schematic view showing a layout of a scintillation crystal array and a photo sensor array according to still another embodiment of the present invention.
Figure 10A:
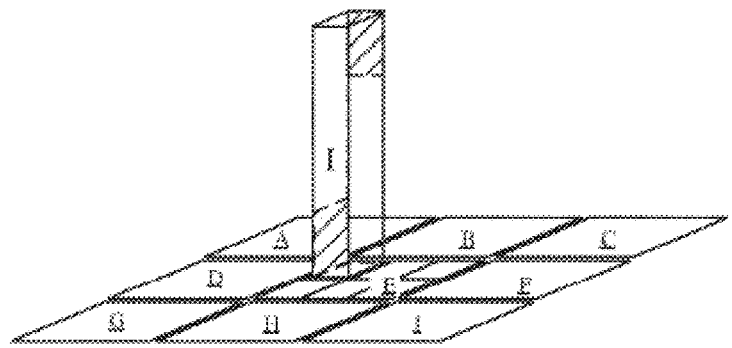
FIGS. 10A-10F are schematic views illustrating DOI decoding in the layout shown in FIG. 9.
Figure 10B:
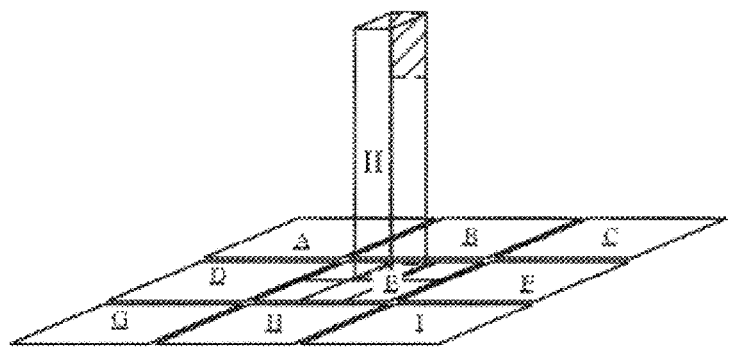
Figure 10C:
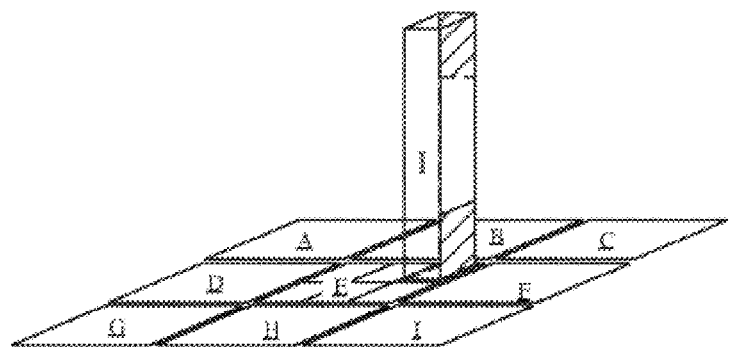
Figure 10D:
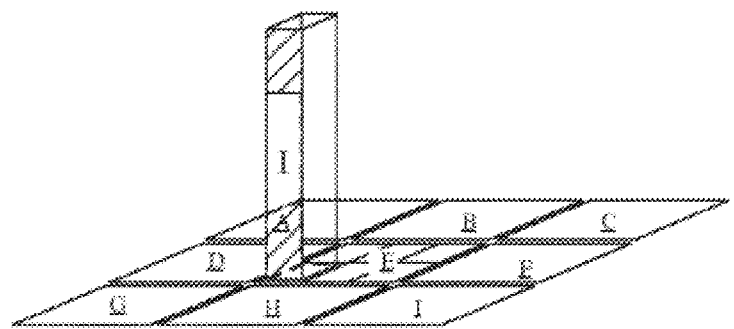
Figure 10E:
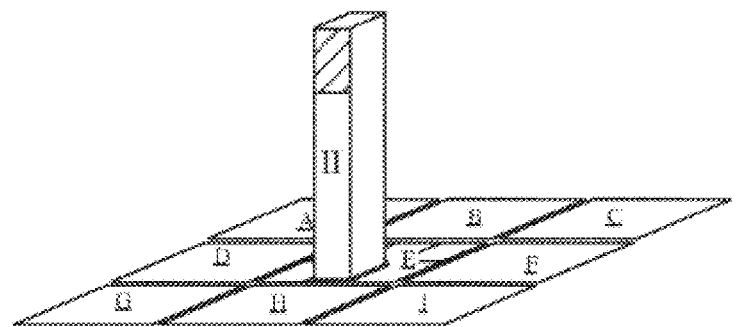
Figure 10F:
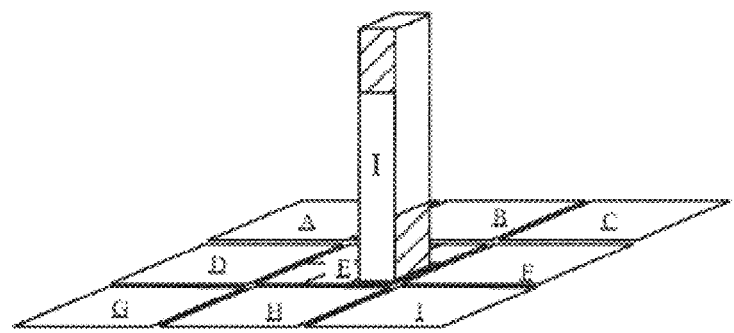

FIG. 9 shows a layout in which one photo sensor is coupled to 2×3 scintillation crystals, wherein the photo sensor array includes 3×3 photo sensors A-I. FIGS. 10A-10F show the decoding for the scintillation crystals coupled to the photo sensor E in the middle of this layout. The decoding for the scintillation crystals coupled to the photo sensors A-D and F-I at the corners and edges is similar to that in the above-described embodiments, and those skilled in the art can understand the decoding for these scintillation crystals with reference to the above description. Also, the sizes of the photo sensors A-D and F-I at the corners and edges may be adjusted according to the sizes of the scintillation crystals coupled to them. Furthermore, the number of the scintillation crystals coupled to the photo sensors A-D and F-I at the corners and edges is also not limited by the drawings. For example, these photo sensors A-D and F-I may also each be coupled to 2×3 scintillation crystals, but some of the scintillation crystals are the third scintillation crystals III, and thus DOI decoding cannot be performed.

The scintillation crystals located at the four corners of the photo sensor E are the first scintillation crystals I. The remaining two scintillation crystals are the second scintillation crystals II. Taking the first scintillation crystal I in the first row and first column as an example, referring to FIG. 10A, the photo sensors A, B, D and E each receives a signal, wherein the signal received by the photo sensor E is the strongest, and the signal received by the photo sensor A is the weakest. The Depth Of Interaction can be derived from the ratio of signals received by the photo sensors A, B, D and E. Taking the second scintillation crystal II in the first row and second column as an example, referring to FIG. 10B, the photo sensors B and E each receives a signal, wherein the signal received by the photo sensor E is stronger, and the signal received by the photo sensor B is weaker. The Depth Of Interaction can be derived from the ratio of signals of the photo sensors B and E. The DOI decoding for the scintillation crystals in the remaining positions may be referred to Table 2.

TABLE 2

| Positions of the scintillation crystals | | Light signals received by the photo sensors | | | | | | | | |
|---|---|---|---|---|---|---|---|---|---|---|
| Row | Column | A | B | C | D | E | F | G | H | I |
| 1 | 1 (FIG. 10A) | weak | moderate | — | moderate | strong | — | — | — | — |
| | 2 (FIG. 10B) | — | weak | — | — | strong | — | — | — | — |
| | 3 (FIG. 10C) | — | moderate | weak | — | strong | moderate | — | — | — |
| 2 | 1 (FIG. 10D) | — | — | — | moderate | strong | — | weak | moderate | — |
| | 2 (FIG. 10E) | — | — | — | — | strong | — | — | weak | — |
| | 3 (FIG. 10F) | — | — | — | — | strong | moderate | — | moderate | weak |

Figure 11:
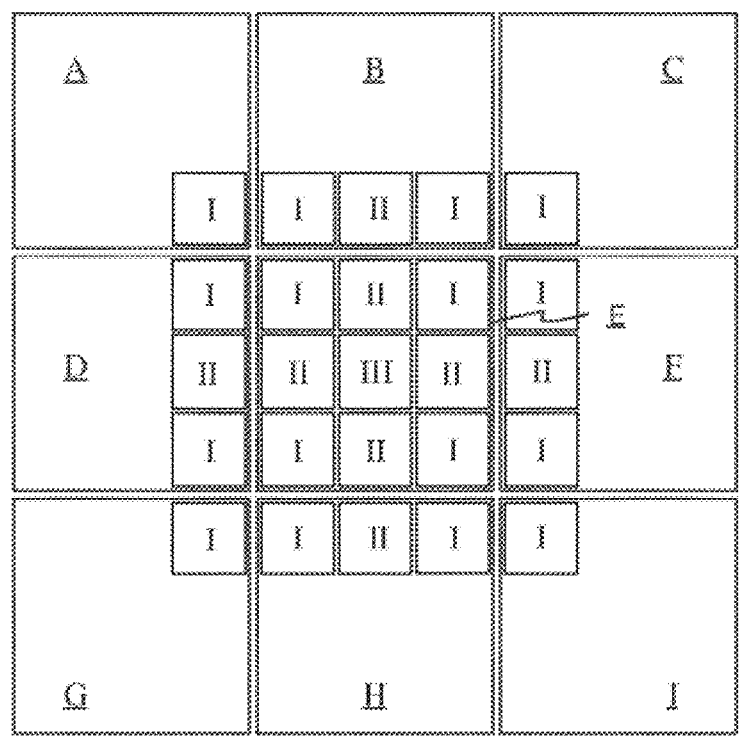
FIG. 11 is a schematic view showing a layout of a scintillation crystal array and a photo sensor array according to yet another embodiment of the present invention.
Figure 12A:
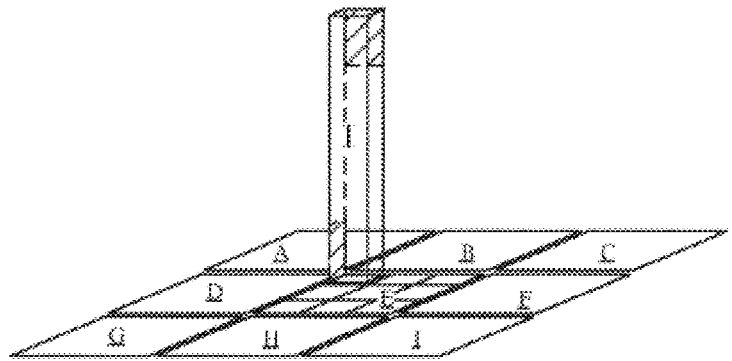
FIGS. 12A-12I are schematic views illustrating DOI decoding in the layout shown in FIG. 11.
Figure 12B:
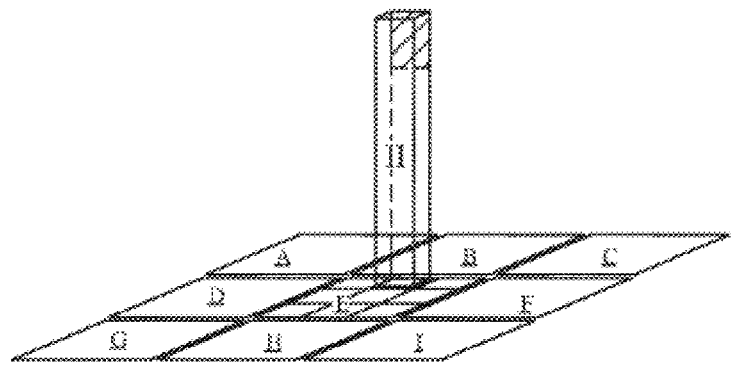
Figure 12C:
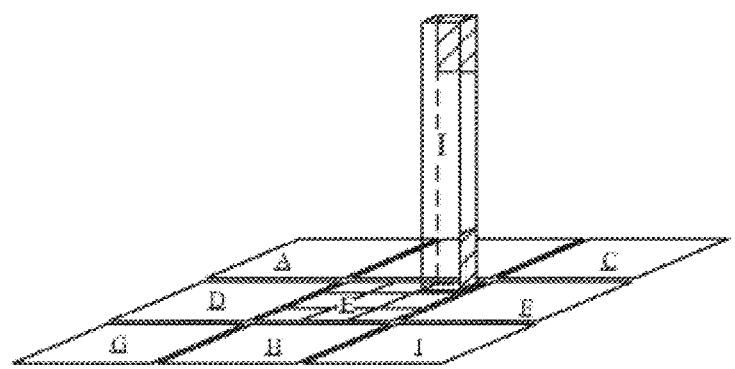
Figure 12D:
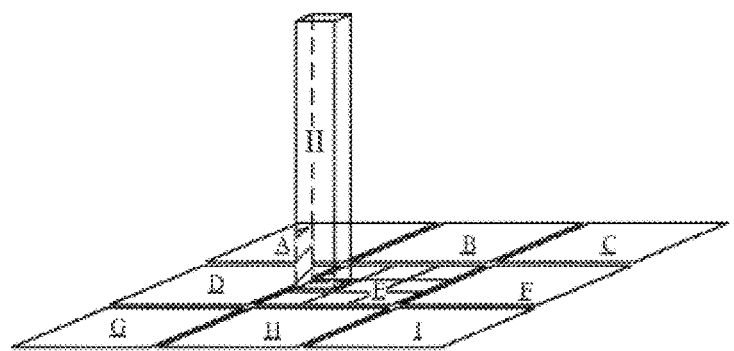
Figure 12E:
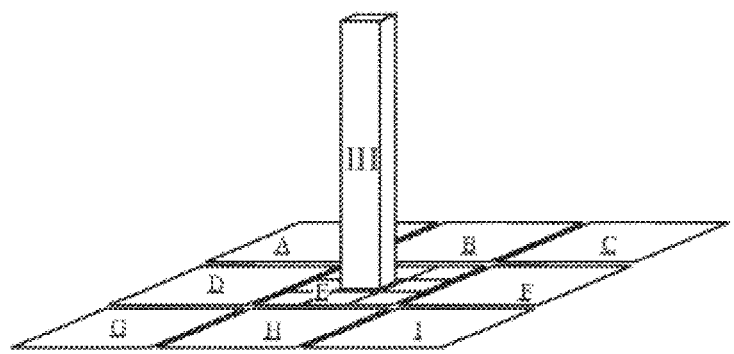
Figure 12F:
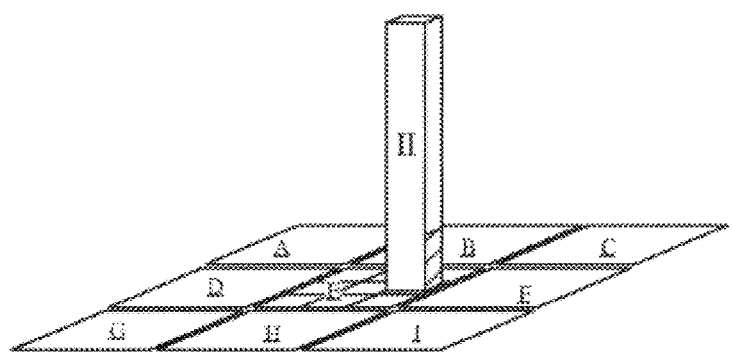
Figure 12G:
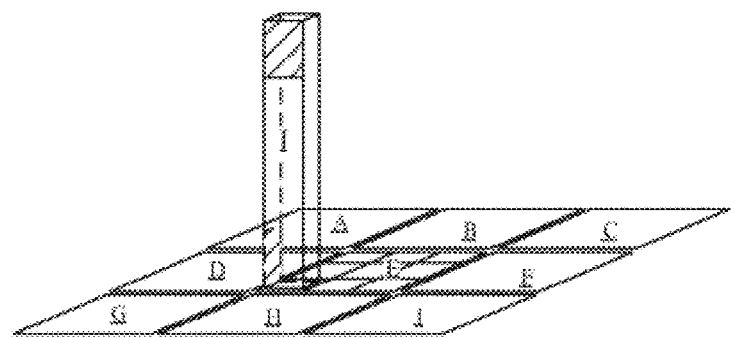
Figure 12H:
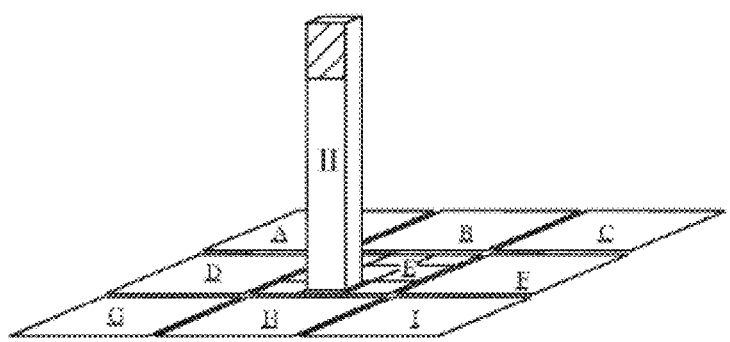
Figure 12I:
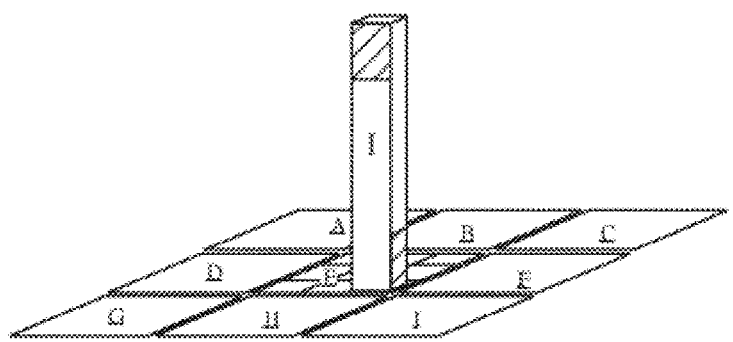

FIG. 11 shows a layout in which one photo sensor is coupled to 3×3 scintillation crystals, wherein the photo sensor array includes 3×3 photo sensors A-I. FIGS. 12A-12I show the decoding for the scintillation crystals coupled to the photo sensor E in the middle of this layout. The decoding for the scintillation crystals coupled to the photo sensors A-D and F-I at the corners and edges is similar to that in the above-described embodiments, and those skilled in the art can understand the decoding for these scintillation crystals with reference to the above description. Also, the sizes of the photo sensors A-D and F-I at the corners and edges may be adjusted according to the sizes of the scintillation crystals coupled to them. Furthermore, the number of the scintillation crystals coupled to the photo sensors A-D and F-I at the corners and edges is also not limited by the drawings. For example, these photo sensors A-D and F-I may also each be coupled to 2×2, 2×3 and/or 3×2 scintillation crystals, and some of the scintillation crystals are the third scintillation crystals III, and thus DOI decoding cannot be performed.

The scintillation crystals located at the four corners of the photo sensor E are the first scintillation crystals I. The four scintillation crystals located at the four edges of the photo sensor E are the second scintillation crystals II. The scintillation crystal located at the center of the photo sensor E is the third scintillation crystal III. Taking the first scintillation crystal I in the first row and first column as an example, referring to FIG. 12A, the photo sensors A, B, D and E each receives a signal, wherein the signal received by the photo sensor E is the strongest, and the signal received by the photo sensor A is the weakest. The Depth Of Interaction can be derived from the ratio of signals received by the photo sensors A, B, D and E. Taking the second scintillation crystal II in the first row and second column as an example, referring to FIG. 12B, the photo sensors B and E each receives a signal, wherein the signal received by the photo sensor E is stronger, and the signal received by the photo sensor B is weaker. The Depth Of Interaction can be derived from the ratio of signals received by the photo sensors B and E. Taking the third scintillation crystal III in the second row and second column as an example, referring to FIG. 12E, the third scintillation crystal III is not adjacent to any photo sensor, and is not provided with any light-transmitting window, and thus DOI decoding cannot be performed. The DOI decoding for the scintillation crystals in the remaining positions may be referred to Table 3.

TABLE 3

| Positions of the scintillation crystals | | Light signals received by the photo sensors | | | | | | | | |
|---|---|---|---|---|---|---|---|---|---|---|
| Row | Column | A | B | C | D | E | F | G | H | I |
| 1 | 1 (FIG. 12A) | weak | moderate | — | moderate | strong | — | — | — | — |
| | 2 (FIG. 12B) | — | weak | — | — | strong | — | — | — | — |
| | 3 (FIG. 12C) | — | moderate | weak | — | strong | moderate | — | — | — |
| 2 | 1 (FIG. 12D) | — | — | — | weak | strong | — | — | — | — |
| | 2 (FIG. 12E) | — | — | — | — | strong | — | — | — | — |
| | 3 (FIG. 12F) | — | — | — | — | strong | weak | — | — | — |
| 3 | 1 (FIG. 12G) | — | — | — | moderate | strong | — | weak | moderate | — |
| | 2 (FIG. 12H) | — | — | — | — | strong | — | — | weak | — |
| | 3 (FIG. 12I) | — | — | — | — | strong | moderate | — | moderate | weak |

In the above-described layout in which various types of the scintillation crystals are coupled, the photo sensor located in the central region of the photo sensor array is coupled to $n_1 \times n_2$ scintillation crystals. Four scintillation crystals among the $n_1 \times n_2$ scintillation crystals located at the corners of the corresponding photo sensor are the first scintillation crystals I. $2(n_1-2)+2(n_2-2)$ scintillation crystals among the $n_1 \times n_2$ scintillation crystals located at the edges of the corresponding photo sensor are the second scintillation crystals II, where $n_1$ and $n_2$ are 2 or 3. The four photo sensors located at the corners of the photo sensor array are each coupled to one first scintillation crystal I. The photo sensors located at the lateral edges of the photo sensor array are each coupled to $n_1 \times 1$ scintillation crystals, and the photo sensors located at the longitudinal edges of the photo sensor array are each coupled to $1 \times n_2$ scintillation crystals, where the scintillation crystals among the $n_1 \times 1$ and $1 \times n_2$ scintillation crystals located at the corners of the corresponding photo sensors are the first scintillation crystals I, and the scintillation crystals among the $n_1 \times 1$ and $1 \times n_2$ scintillation crystals located at the edges of the corresponding photo sensors are the second scintillation crystals II.

Furthermore, the scintillation crystals coupled to a single photo sensor may also be extended to $n_1 \times 1$ or $1 \times n_2$, where $n_1$ and $n_2$ are 2 or 3. In a row or column of scintillation crystals, the scintillation crystals at both ends are the first scintillation crystals I, and the $(n_1-2)$ or $(n_2-2)$ crystals located in the middle of the corresponding photo sensor are the second scintillation crystals II. When $n_1$ or $n_2$ is 2, there is no scintillation crystal located in the middle of the corresponding photo sensor.

According to another aspect of the present invention, there is further provided an emission tomography device, and the emission tomography device includes a kind of the detectors as described above.

In the detector provided by the present invention, the scintillation crystal array is directly coupled to the photo sensor array, and at least some of the photo sensors are coupled to a plurality of scintillation crystals. Since light-transmitting windows are disposed on the surfaces on the adjacent scintillation crystals coupled to the adjacent photo sensors, DOI decoding can be performed for the scintillation crystals by means of using two or four adjacent photo sensors. No mutual interference occurs during DOI decoding, and decoding is more accurate. Also, with the number of photo sensor arrays being the same, the two-dimensional and DOI decoding capability for the scintillation crystals is significantly improved. For example, the decoding capability is improved by 4 times in the layout shown in FIGS. 5A-5B, the decoding capability is improved by 6 times in the layout shown in FIG. 9, and the decoding capability is improved by 9 times in the layout shown in FIG. 11. Therefore, with the number of photo sensor arrays being the same, the size of the photo sensor array of the present invention can be reduced by three-quarters to eight-ninths, and the number of channels of a readout circuit of the photo sensors can also be reduced by three-quarters to eight-ninths.

The present invention has been described by the above-described embodiments, but it should be understood that, the above-described embodiments are only for the purpose of illustration and description, and are not intended to limit the present invention within the scope of the described embodiments. Furthermore, those skilled in the art can understand that, the present invention is not limited to the above-described embodiments, and various variations and modifications can be made according to the teachings of the present invention. These variations and modifications all fall within the scope of protection of the present invention. The scope of protection of the present invention is defined by the appended claims and their equivalents.

The invention claimed is:

1. A detector for an emission tomography device, comprising:
    a scintillation crystal array comprising a plurality of scintillation crystals;
    a photo sensor array, coupled to an end surface of the scintillation crystal array and comprising multiple photo sensors, wherein at least one of the multiple photo sensors is coupled to a plurality of the scintillation crystals respectively;
    wherein surfaces of the plurality of the scintillation crystals not coupled to the photo sensor array are each provided with a light-reflecting layer, and a light-transmitting window is disposed in the light-reflecting layer on a surface among the surfaces adjacent to a scintillation crystal coupled to an adjacent photo sensor,
    wherein each of the plurality of the scintillation crystals has other surfaces which are adjacent to a scintillation crystal coupled to a same photo sensor and no light-transmitting window is disposed in the light-reflecting layer on the other surfaces, and wherein two adjacent surfaces of the other surfaces intersect at a first ridge which abuts second ridges of the scintillation crystals coupled to the same photo sensor, and no light-transmitting window is disposed in light-reflecting layers on surfaces which intersect at the second ridges.

2. The detector according to claim 1, wherein the plurality of the scintillation crystals comprises a first scintillation crystal(s), and each of the first scintillation crystal(s) has two surfaces which are adjacent to other first scintillation crystals coupled to adjacent photo sensors; and wherein the light-transmitting window comprises a first light-transmitting window and a second light-transmitting window which are respectively disposed in the light-reflecting layers on the two surfaces of the first scintillation crystal to allow light to be received by adjacent photo sensors.

3. The detector according to claim 2, wherein $m_1 \times m_2$ photo sensors located in the central region of the photo sensor array are each coupled to $n_1 \times n_2$ first scintillation crystals, wherein $m_1$ and $m_2$ are each a positive integer, and wherein $n_1$ and $n_2$ are 1 or 2, and $n_1$ and $n_2$ are not equal.

4. The detector according to claim 3, wherein four photo sensors located at the corners of the photo sensor array are each coupled to one first scintillation crystal.

5. The detector according to claim 3, wherein $2m_1$ photo sensors located at the lateral edges of the photo sensor array are each coupled to $n_1 \times 1$ first scintillation crystals, and $2m_2$ photo sensors located at the longitudinal edges of the photo sensor array are each coupled to $1 \times n_2$ first scintillation crystals.

6. The detector according to claim 2, wherein the plurality of the scintillation crystals further comprises a second scintillation crystal(s), and each of the second scintillation crystal(s) has one surface which is adjacent to a scintillation crystal coupled to an adjacent photo sensor, and a light-transmitting window is disposed on the one surface of the second scintillation crystal to allow light to be received by the adjacent photo sensor.

7. The detector according to claim 6, wherein photo sensors located in the central region of the photo sensor array are each coupled to $n_1 \times n_2$ scintillation crystals, and four scintillation crystals among the $n_1 \times n_2$ scintillation crystals located at corners of a corresponding photo sensor are the first scintillation crystals, and $2(n_1-2)+2(n_2-2)$ scintillation crystals among the $n_1 \times n_2$ scintillation crystals located at the edges of the corresponding photo sensor are the second scintillation crystals, wherein $n_1$ and $n_2$ are 2 or 3.

8. The detector according to claim 7, wherein the four photo sensors located at the corners of the photo sensor array are each coupled to one first scintillation crystal.

9. The detector according to claim 7, wherein photo sensors located at the lateral edges of the photo sensor array are each coupled to $n_1 \times 1$ scintillation crystals, and photo sensors located at the longitudinal edges of the photo sensor array are each coupled to $1 \times n_2$ scintillation crystals, and wherein scintillation crystals among the $n_1 \times 1$ scintillation crystals and the $1 \times n_2$ scintillation crystals located at corners of a corresponding photo sensor are the first scintillation crystals, and scintillation crystals among the $n_1 \times 1$ scintillation crystals and the $1 \times n_2$ scintillation crystals located at the edges of a corresponding photo sensor are the second scintillation crystals.

10. The detector according to claim 6, wherein the photo sensors in the photo sensor array are each coupled to $n_1 \times 1$ or $1 \times n_2$ scintillation crystals, and scintillation crystals located at both ends of a corresponding photo sensor are the first scintillation crystals, and $(n_1-2)$ or $(n_2-2)$ scintillation crystals located in the middle of a corresponding photo sensor are the second scintillation crystals, wherein $n_1$ and $n_2$ are 2 or 3, and $n_1$ and $n_2$ are not equal.

11. The detector according to claim 6, wherein the light-transmitting window of the second scintillation crystal is disposed away from the photo sensor array.

12. The detector according to claim 1, wherein the plurality of the scintillation crystals further comprise a third scintillation crystal(s), and the third scintillation crystal(s) is not adjacent to any scintillation crystal coupled to an adjacent photo sensor, and the third scintillation crystal(s) is located at the corners of the scintillation crystal array, and/or located at the middle region of a photo sensor in the middle region.

13. An emission tomography device, wherein the emission tomography device comprises the detector according to claim 1.

* * * * *